US00PP19561P2

(12) United States Plant Patent
Poe

(10) Patent No.: US PP19,561 P2
(45) Date of Patent: Dec. 9, 2008

(54) ***ABIES FRASERI* PLANT NAMED 'FROSTY'**

(50) Latin Name: *Abies fraseri*
Varietal Denomination: Frosty

(76) Inventor: Kent Poe, 1756 Frank Dillard Rd., Jefferson, NC (US) 28460

( * ) Notice: Subject to any disclaimer, the term of this patent is extended or adjusted under 35 U.S.C. 154(b) by 0 days.

(21) Appl. No.: 12/004,762

(22) Filed: Dec. 21, 2007

(51) Int. Cl.
*A01H 5/00* (2006.01)

(52) U.S. Cl. ..... Plt./213

(58) Field of Classification Search ..... Plt./213
See application file for complete search history.

*Primary Examiner*—Annette H Para
(74) *Attorney, Agent, or Firm*—Myers Bigel Sibley & Sajovec, P.A.

(57) ABSTRACT

*Abies fraseri* 'Frosty' is distinguishable from other varieties of *Abies fraseri* primarily by its distinctive blue white needle color. 'Frosty' also exhibits a slightly shorter needle length and the needles are more crowded on the branch giving the new variety a more dense appearance than a typical Fraser fir tree. In addition, 'Frosty' produces more lateral limbs on the tree terminal resulting in thicker branches as compared to a typical Fraser fir.

7 Drawing Sheets

Latin name of the genus and species: The Latin name of the novel, ornamental plant variety disclosed herein is *Abies fraseri* (Pursh) Poir.

Variety denomination: The inventive cultivar of *Abies fraseri* disclosed herein has been given the varietal denomination 'Frosty'.

BACKGROUND OF THE INVENTION

The present invention relates to a new and distinct variety of *Abies fraseri* named 'Frosty'. This variety is distinguishable from other *Abies fraseri* varieties primarily by its distinctive blue white needle color.

Lineage. The *Abies fraseri* 'Frosty' cultivar was discovered as a two-year old seedling growing in a cultivated area on the Poe Tree Farm in Jefferson, N.C. in 1992; thus, its parentage is unknown. The single, individual plant now known as *Abies fraseri*, 'Frosty' was identified due to its exceptional feature of blue white needle color (FIG. 1). The seedling was protected from rodents and mice by a screen wire cage and allowed to grow for an additional three years receiving only a light mulch of pine needles for winter protection. The original plant is now seventeen years old and has maintained its distinctive blue white needle color (FIG. 2).

Asexual Reproduction. The new and distinct variety, *Abies fraseri* 'Frosty' was first asexually reproduced in 2005 in Jefferson, N.C. by grafting onto rootstock of *Abies fraseri* (FIGS. 3–5). While the majority of grafts made since that time have been on rootstock of A. fraseri, grafts have also been made on rootstock of *Abies firma* (Momi Fir) (FIG. 6). The typical grafting procedure involves making a simple cleft graft on the terminal of five year old Fraser fir tree and then uniting the scion and rootstock using rubber bands and grafting wax. In 2007, a polyfilm was successfully substituted for the rubber bands and grafting wax. All grafts have retained the distinctive blue white needle color of the original parent tree. Thus, the distinctive characteristics of the new cultivar have remained stable and reproduce true to type in successive generations of asexual reproduction.

SUMMARY OF THE INVENTION

*Abies fraseri* 'Frosty' is distinguishable from other varieties of *Abies fraseri* primarily by its distinctive blue white needle color. 'Frosty' also exhibits a slightly shorter needle length and the needles are more crowded on the branch giving the new variety a more dense appearance than a typical Fraser fir tree. In addition, 'Frosty' produces more lateral limbs on the tree terminal resulting in thicker branches as compared to a typical Fraser fir.

BRIEF DESCRIPTION OF THE DRAWINGS

The photographs in the drawings were made using conventional techniques and show the colors as true as reasonably possible by conventional photography. Colors in the photographs may differ slightly from the color values cited in the detailed botanical description, which accurately describe the colors of the new *Abies fraseri.*

DETAILED BOTANICAL DESCRIPTION

Figure 1:
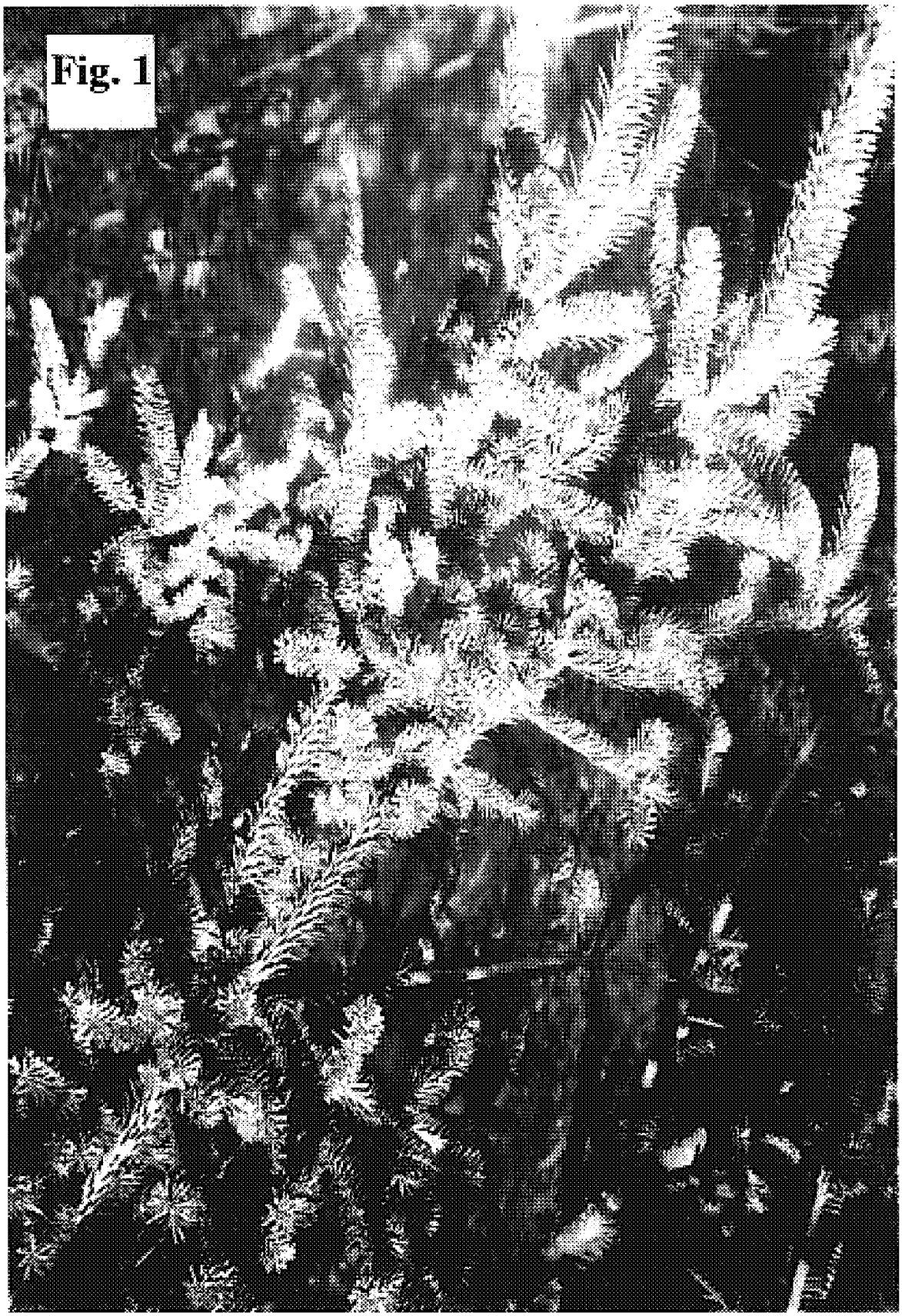
FIG. 1 is a color photograph showing a close up of the new variety *Abies fraseri* 'Frosty'.
Figure 2:
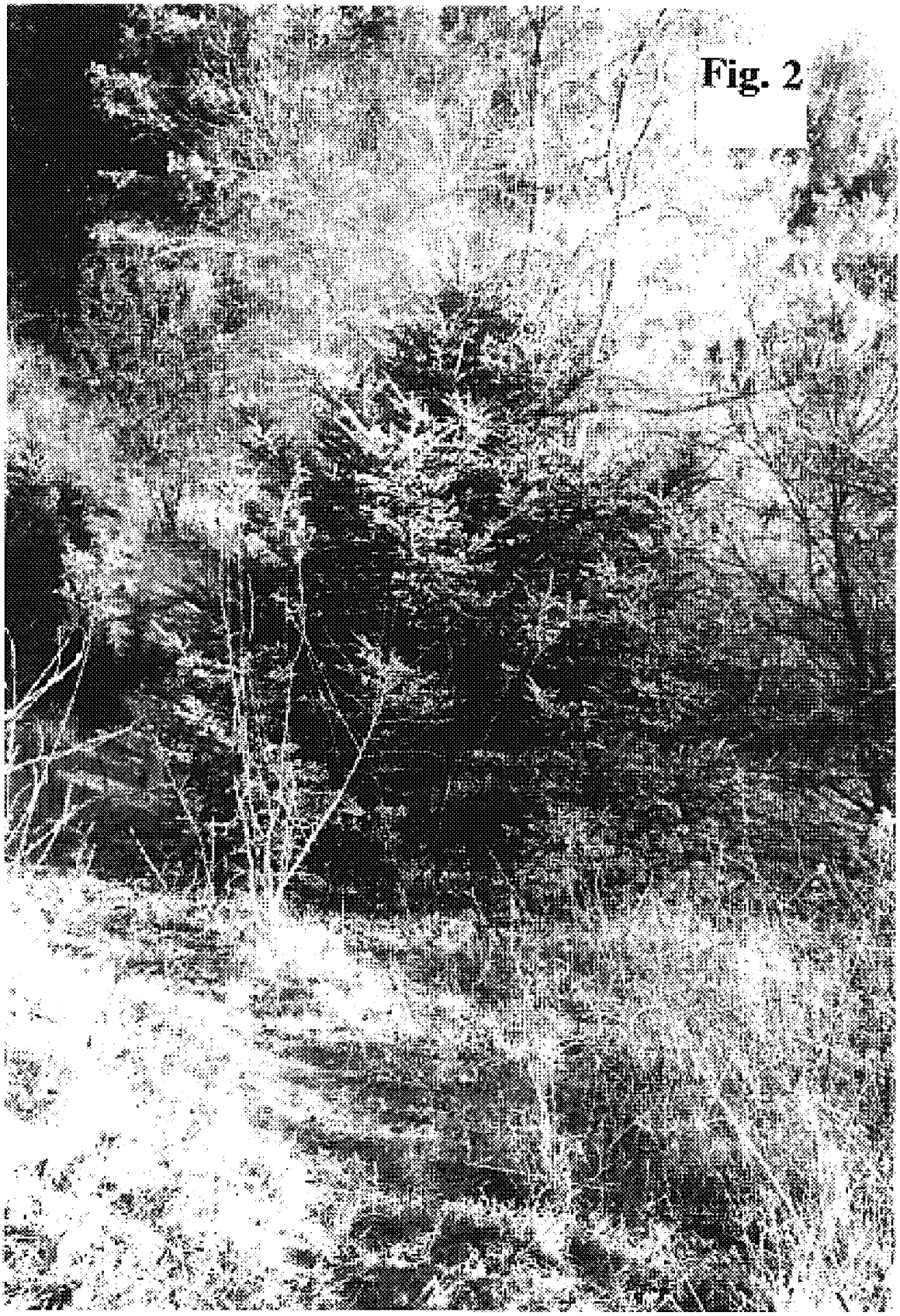
FIG. 2 is a color photograph showing the seventeen-year old parent tree of the variety *Abies fraseri* 'Frosty' on the Poe Tree Farm.
Figure 3:
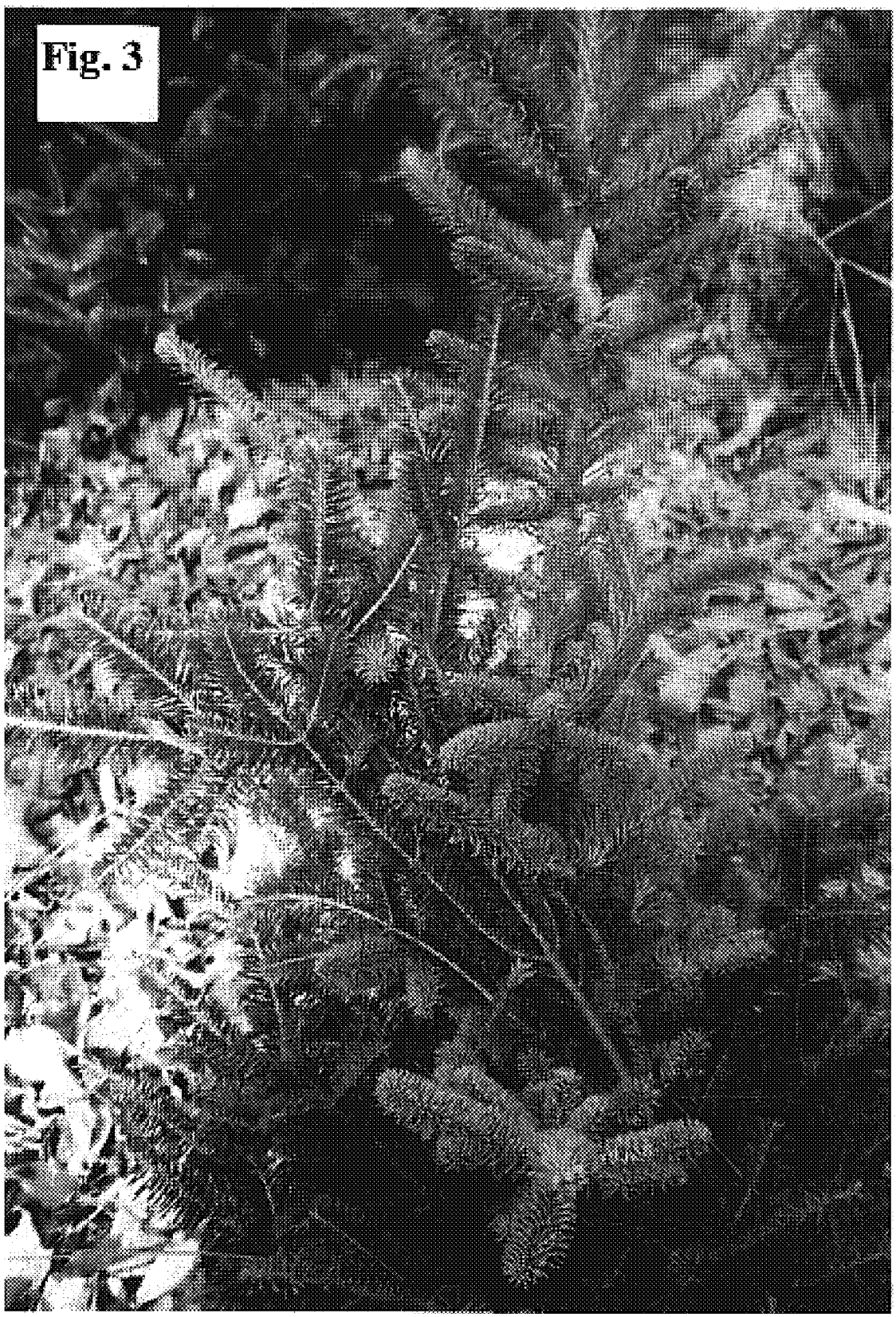
FIG. 3 is a color photograph showing a three-year old graft of the variety *Abies fraseri* 'Frosty'.
Figure 4:
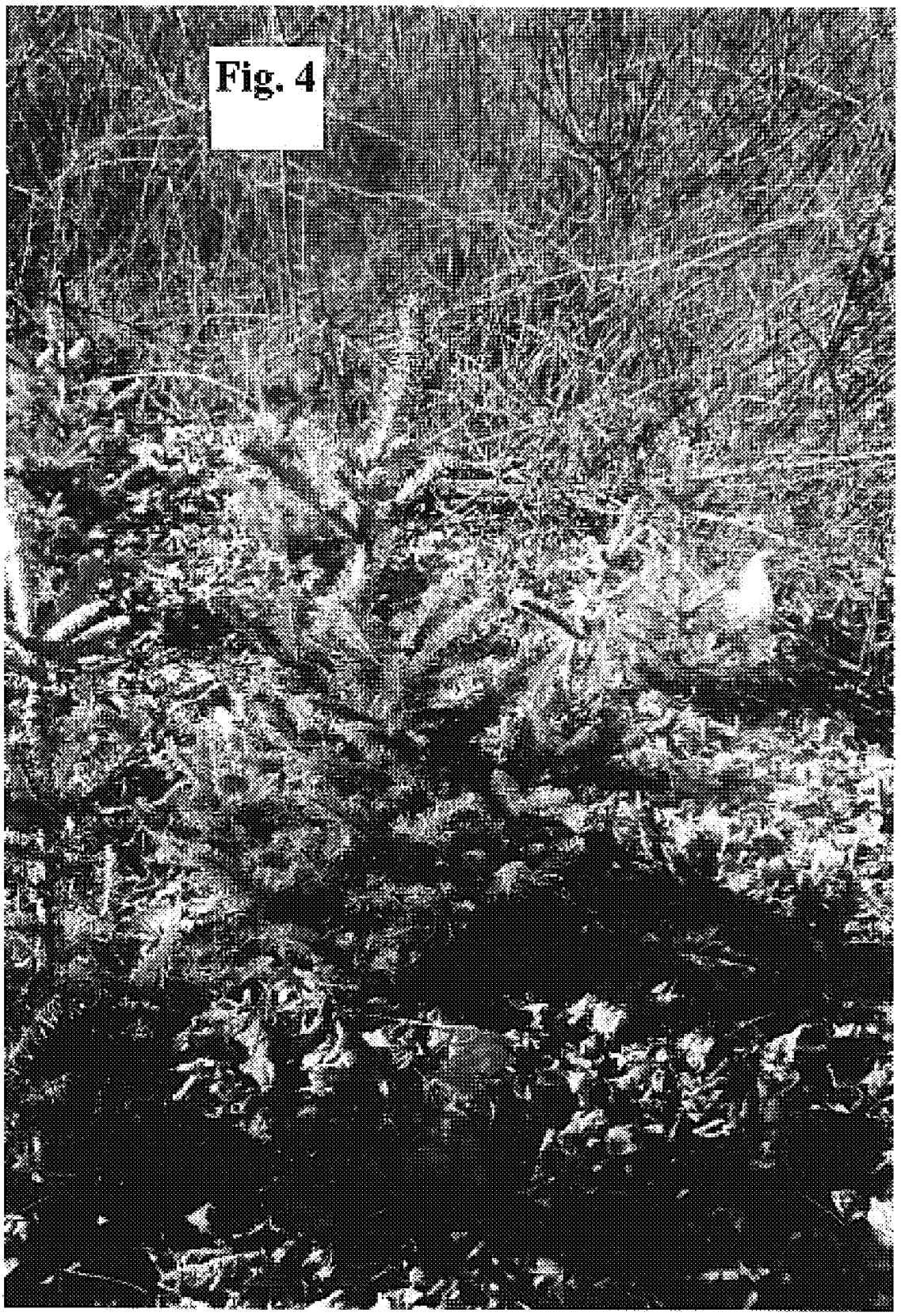
FIG. 4 is a color photograph showing a two-year old graft of the variety *Abies fraseri* 'Frosty' on *Abies fraseri* rootstock.
Figure 5:
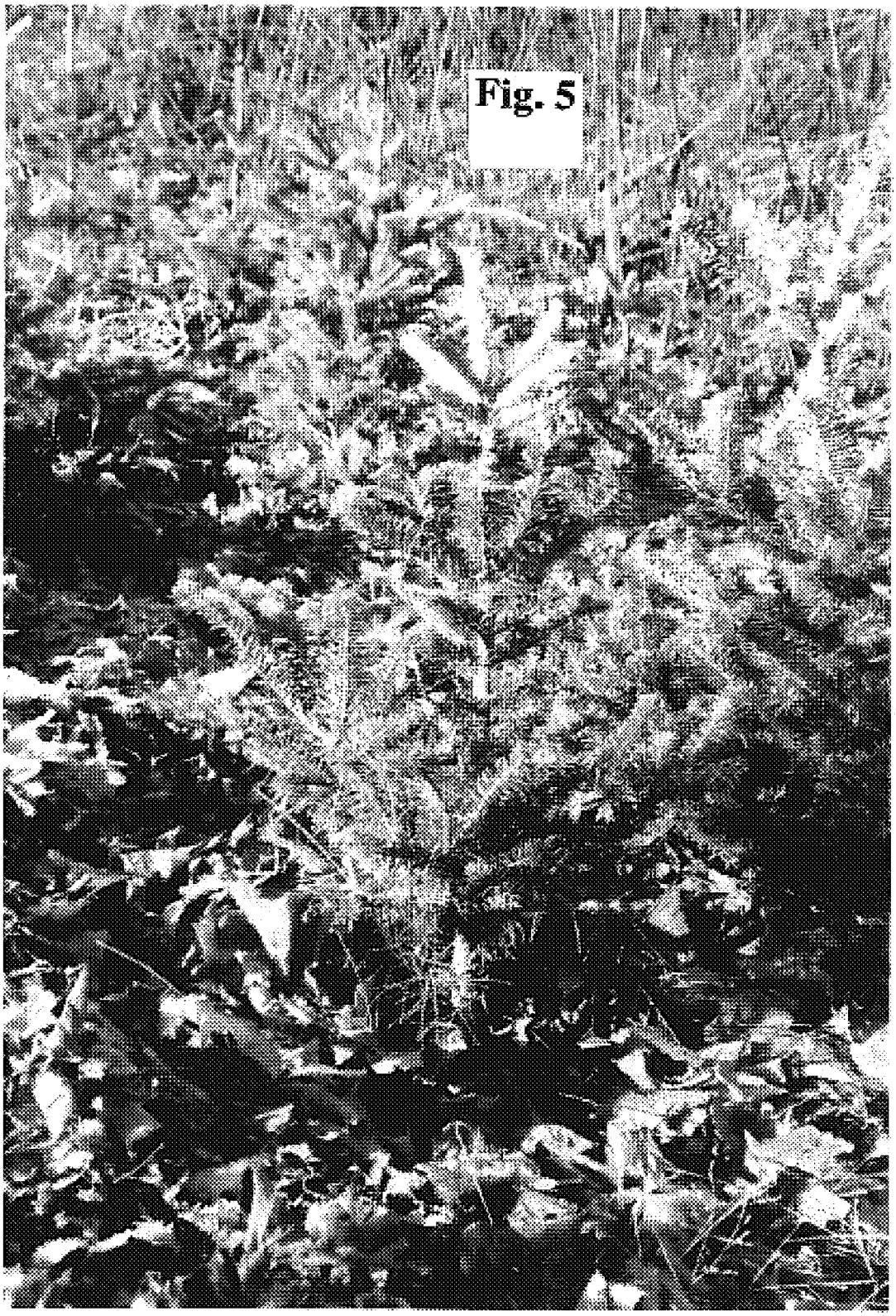
FIG. 5 is a color photograph showing a one-year old graft of the variety *Abies fraseri* 'Frosty' on *Abies fraseri* rootstock.
Figure 6:
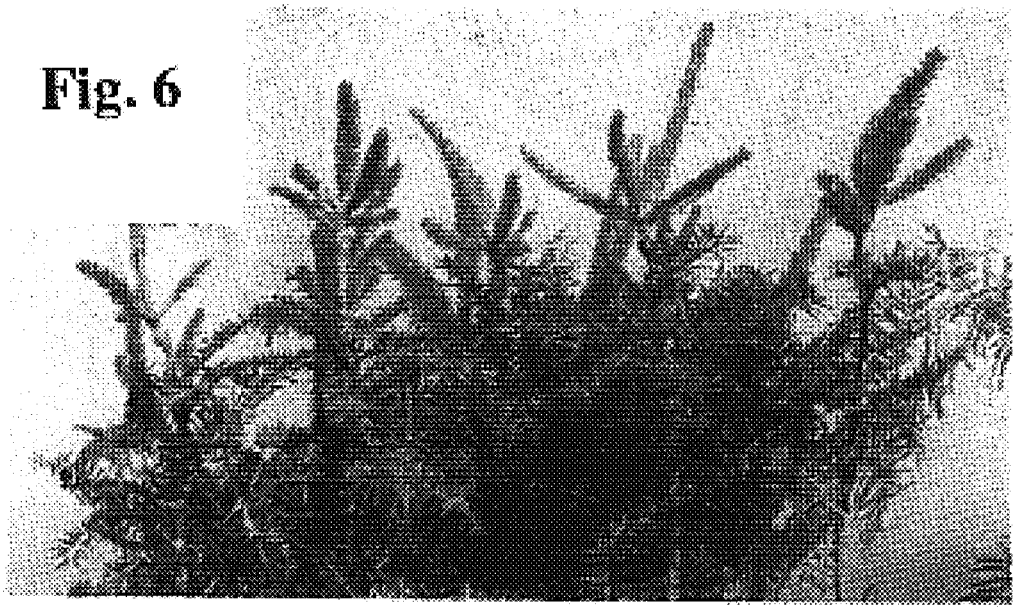
FIG. 6 is a color photograph showing grafts of the variety *Abies fraseri* 'Frosty' on *Abies firma* rootstock.

The following is a detailed description of the botanical characteristics of the new and distinct cultivar of *Abies fraseri* plant known by the denomination 'Frosty'. All colors cited herein refer to The Royal Horticultural Society Colour Chart (The Royal Horticultural Society, London, 2001 edition) designations except where general terms of ordinary dictionary significance are used. Where dimensions, sizes, colors, and other characteristics are given, it is to be understood that such characteristics are approximations or averages set forth as accurately as practicable.

The descriptions reported herein are from the 17 year-old parent tree. Those skilled in the art will appreciate that certain characteristics will vary with older or, conversely, younger plants. *Abies fraseri* 'Frosty' has not been observed under all possible environmental conditions. Where dimensions, sizes, colors and other characteristics are given, it is to be understood that such characteristics are approximations or averages set forth as accurately as practicable. The phenotype of the variety may differ with variations in the environment such as season, temperature, light intensity, day length, cultural conditions and the like.

Technical Description of the Variety

Plant:

*Shape*.—The natural shape of the new variety is pyramidal.

*Height*.—4.5 meters at 15 years of age. Mature height and age unknown.

*Diameter*.—5.6 m at bottom branches.

*Growth rate*.—Slightly slower than the typical *Abies fraseri*.

Roots: Shallow, fibrous root system, older growth is grey orange (RHS 174A), while newer growth is creamy white.

Trunk:

*Diameter*.—Trunk is 24 cm in diameter at ground level tapering to 16 cm in diameter at 90 cm in height.

*Texture*.—Smooth with knots on the bark, which contain resin, making for a lumpy appearance.

*Color*.—Brown (RHS N200B) with blotches of grey white.

Branches:

*Habit*.—Older branches at the base of the tree exit the tree at about a 90° angle, then gently slope downward to touch the ground, then curve slightly upward to leave the limb tips at about 40 cm above ground level. Branches nearer the top of the tree leave the tree at about a 60° angle then tend to bend into a position leaving the tips pointed upward toward the top of the tree.

*Length and diameter*.—Lower branches are about 2.8 m in length. Limbs gradually become shorter as they go up the trunk to give the tree a pyramidal shape. The diameter of the limbs at the base is about 7 cm with diameter decreasing as the limbs go higher on the tree.

*Foliage*.—Needles crowded, directed forward, 10–18 mm long, 1 mm wide, blue white color: upper surface (RHS 112B), lower surface (RHS 112C).

*Cones*.—Ovoid or cylindrical, 3–5 cm long, 2 cm wide, greenish purple before maturity, turning brown (RHS 200C) at maturity.

*Seed*.—5 mm in length, 3 mm wide, wing 8 mm in length, 4 mm wide, grey (RHS 200A) in color.

Growth conditions. *Abies fraseri* 'Frosty' has been grown and observed for a period of fifteen years in Jefferson, N.C., Ashe County. The elevation of Jefferson, N.C. is about 3200 feet above sea level. Summer temperatures in this locale seldom exceed 90°F.; winter temperatures may fall to about 0° F. for short periods time with significantly lower wind chill factors. The soil is a deep loam.

Disease or pest resistance. No notable differences between 'Frosty' and the typical Fraser fir with regard to disease or pest resistance or susceptibility.

Comparison with Other *Abies fraseri* Cultivars

Figure 7:
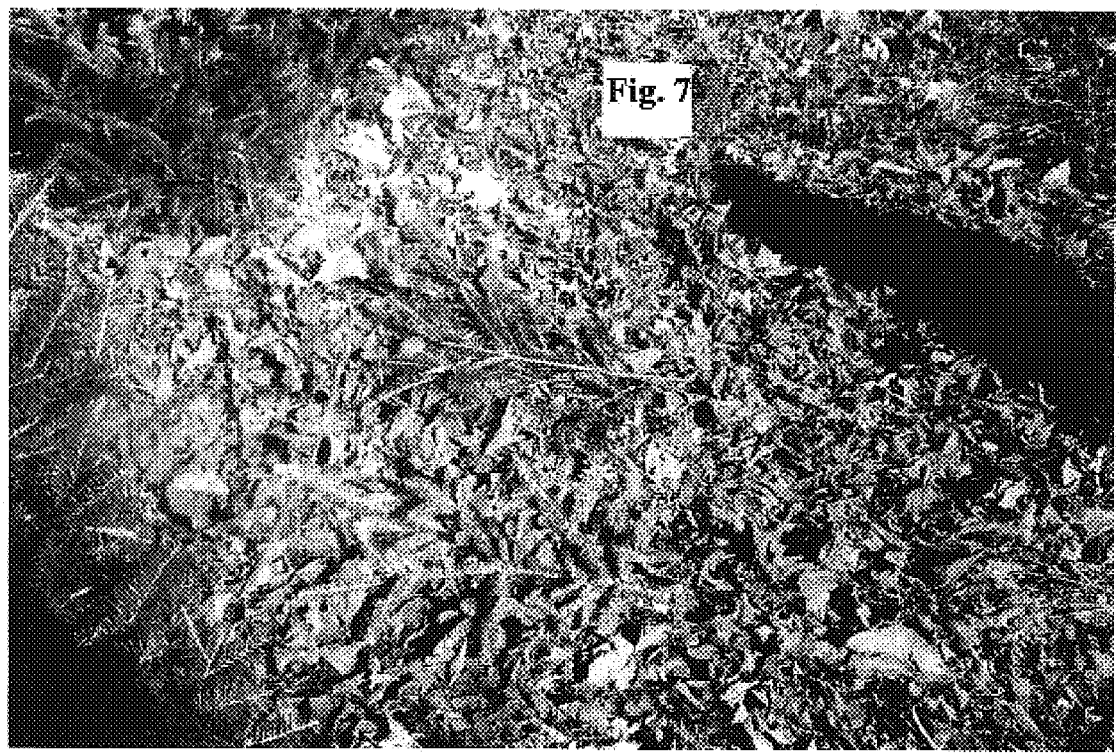
FIG. 7 is a color photograph showing a limb of the new variety *Abies fraseri* 'Frosty' adjacent to a limb of a typical *Abies fraseri.*

'Frosty' is very distinct based on needle color, needle size and number of lateral limbs. (Table 1). The most distinctive characteristic of 'Frosty' is the needle color, which is a blue white (upper side, RHS 112B; lower side, RHS 112C) as compared to green (RHS 132A) for a typical Fraser fir (FIG. 7). Further, the new variety 'Frosty' has slightly shorter needles (10–18 mm) than those of the average Fraser fir (12–20 mm). The needles of 'Frosty' are also more compacted on the branch resulting in a more dense appearance for 'Frosty' than a typical Fraser fir. In addition, *Abies fraseri* 'Frosty' has a greater number of lateral limbs resulting in thicker branches on the tree than is typical for a Fraser fir. An average of 18 lateral buds are found in the top 20 cm of a three-year old graft of 'Frosty' as compared to an average of 10 lateral buds for a typical *Abies fraseri* grown under the same environmental conditions. These comparisons are also presented in Table 1 below.

TABLE 1

| Characteristic | New Variety 'Frosty' | Typical Fraser fir |
|---|---|---|
| Foliage Color | | |
| Upper | Blue white (RHS 112B) | Green (RHS 132A) |
| Lower | Blue white (RHS 112C) | Green (RHS 132A) |
| Needle Length | 10-18 mm | 12-20 mm |
| Number of Lateral buds | 18 | 10 |

What is claimed is:

1. A new and distinct cultivar of *Abies fraseri* plant named 'Frosty', substantially as illustrated and described herein.

* * * * *